United States Patent
Jones et al.

[11] 3,935,184
[45] Jan. 27, 1976

[54] SYNTHETIC POLYOXIN TYPE NUCLEOSIDES

[75] Inventors: Gordon H. Jones, Palo Alto; John G. Moffatt, Los Altos; Michael D. Edge, Mountain View, all of Calif.

[73] Assignee: Syntex (U.S.A.) Inc., Palo Alto, Calif.

[22] Filed: Feb. 22, 1972

[21] Appl. No.: 228,366

[52] U.S. Cl... 260/211.5 R; 260/210 R; 260/211 R; 260/234 R; 424/180
[51] Int. Cl.² ............ C07H 19/16; C07H 19/18; C08B 37/00
[58] Field of Search ..... 260/210 R, 234 R, 211.5 R, 260/211 R

[56] References Cited
UNITED STATES PATENTS

| | | | |
|---|---|---|---|
| 3,208,997 | 9/1965 | Iwai et al. | 260/211.5 R |
| 3,328,388 | 6/1967 | Shen et al. | 260/211.5 R |
| 3,380,996 | 4/1968 | Honjo et al. | 260/211.5 R |
| 3,431,252 | 3/1969 | Walton et al. | 260/211.5 R |
| 3,809,689 | 5/1974 | Damodaran et al. | 260/211.5 R |

OTHER PUBLICATIONS
Chu et al., Canadian Journal of Chemistry Vol. 48, 1970 pp. 2306–2309.

Primary Examiner—Johnnie R. Brown
Attorney, Agent, or Firm—Lawrence S. Squires; William B. Walker

[57] ABSTRACT
A novel class of intermediates from which a variety of uronic acid nucleosides can be produced, said class being represented by the following formula:

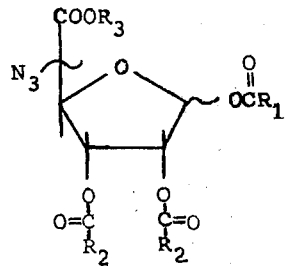

where
$R_1$ and $R_2$ are lower alkyl radicals having one to six carbon atoms, or phenyl radicals;
$R_3$ is a lower alkyl radical having one to four carbon atoms; and the wavy line at the 5' position indicates both the 5'-D-allo and 5'-L-talo epimers.

A process for producing these intermediates is described. A process for converting these intermediates to uronic acid nucleosides having the following formula:

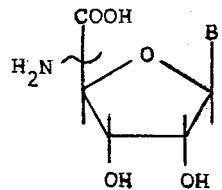

where
B is a pyrimidine or purine base, is also described.
Novel uronic acid nucleosides, having structures falling within the general formula given above, are identified.

16 Claims, No Drawings

SYNTHETIC POLYOXIN TYPE NUCLEOSIDES

BACKGROUND OF THE INVENTION

This application relates to uronic acid nucleosides. Additionally, this application relates to methods for preparing such compounds, including the preparation of a class of general intermediates from which, by process steps described herein, a variety of uronic acid nucleosides can be readily produced. Novel uronic acid nucleosides are described.

In copending application Ser. No. 119,019, filed Feb. 25, 1971, now U.S. Pat. No. 3,809,689, and assigned to the assignee of the present invention, there is disclosed, inter alia, a class of nucleosides having the general formulae:

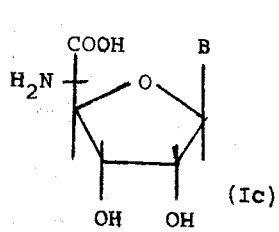
(Ic)

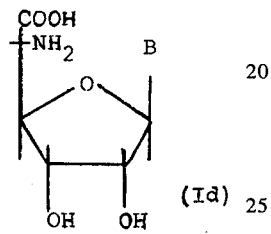
(Id)

where B is selected from various pyrimidine or purine bases identified therein.

The designations Ic and Id represent the β-D-allo and the α-L-talo epimers in which the 5′-amino groups have the opposite configurations. These designations are as given in the aforementioned copending application and will be followed in this application to enable easier review, comparison and understanding of these two related applications.

On pages 20–26 of the specification of the aforementioned copending application there is described, in detail, a process for preparing the compounds of formulae Ic and Id. A schematic flow chart of that process is given on pages 20–21 thereof. This process, though quite capable of being used, as indicated, to produce the compounds of formulae Ic and Id, is not totally satisfactory since the process requires careful tailoring of the starting compound (Z) in view of the particular nucleoside desired, and because the strongly acidic conditions necessary to effect hydrolysis of the amide function to a carboxylic acid would result in almost complete hydrolysis of the intermediate nucleoside to the corresponding sugar when applied to purine derivatives. Since the process is limited by the exclusion of steps which include highly acidic conditions, it is correspondingly limited in the nucleosides which can be produced therewith. Accordingly, it would be desirable to have a more general process for producing the nucleosides of formulae Ic and Id, such process including the preparation of a class of general intermediates from which many nucleosides (having a structure represented by either formula Ic or Id) can be readily prepared in only a few steps.

SUMMARY OF THE INVENTION

A process satisfying the aforementioned general requirements has been developed. This process includes the steps of converting a general intermediate having the formula:

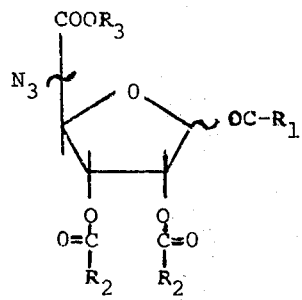

where
$R_1$ is a lower alkyl radical having one to six carbon atoms, or phenyl or a substituted phenyl radical;
$R_2$ is as defined above with regard to $R_1$;
$R_3$ is a lower alkyl radical having one to four carbon atoms; and the wavy line at the 5′ position indicates the 5′-D-allo and 5′-L-talo epimers;

to the corresponding purine or pyrimidine glycosides, converting the 5′azido group in the purine or pyrimidine glycoside to the corresponding 5′-amino derivative, and hydrolysis of the 2′, 3′ and 6′ protecting groups to thereby convert the 5′-amino-purine or 5′-amino-pyrimidine nucleoside to the corresponding uronic acid nucleoside. As the general intermediates identified above (i.e., compounds I or I' below) can be either in the D-allo or L-talo form, the finally derived uronic acid nucleoside will be in either the β-D-allo or α-L-talo form, depending upon the initial general intermediate selected for use in the process of this invention and not upon the particular process steps employed, such steps, and the alternate steps, being described in greater detail below.

A process for preparing the above-identified general intermediate from a commercially available compound (i.e., compound A below) is also described.

The purine uronic acid nucleosides and the pyrimidine uronic acid nucleosides which can be produced according to the process of this invention have the following general formulae:

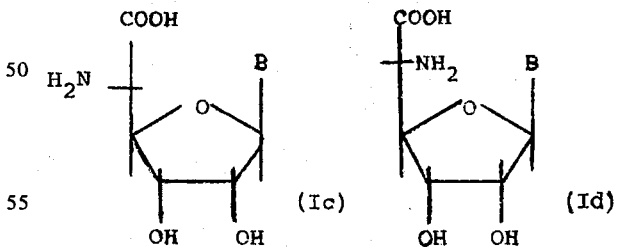

where
B is a pyrimidine base radical selected from the group of radicals having the following formulae:

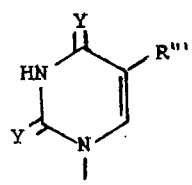 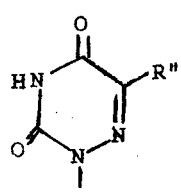 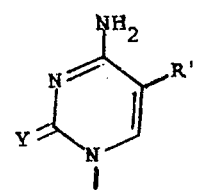

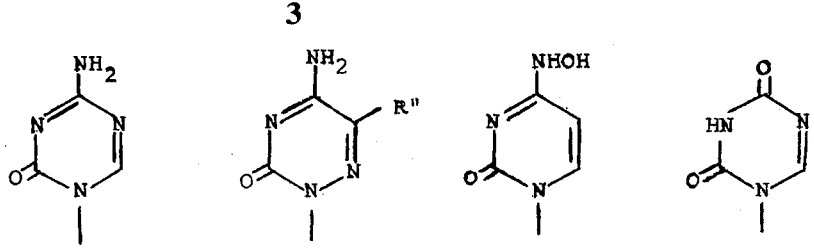

wherein

R' or R''' is H, fluoro, chloro, bromo, iodo, lower alkyl, trifluoromethyl, hydroxymethyl, nitro, amino, methylamino, dimethylamino, and hydroxy;

R'' is H or methyl; wherein the compound of Ic, R''' is fluoro, chloro, bromo, iodo, lower alkyl having from two through seven carbon atoms, amino, trifluoromethyl, nitro, methylamino, dimethylamino, and hydroxy; and Y is either oxo or thio, but when a base radical has two Y groups, one is oxo and the other is thio:

or a purine base radical selected from the group of adenin-9-yl, 2-fluoroadenin-9-yl, 2-azaadenin-9-yl, 6-chloropurin-9-yl, 2,6-dichloropurin-9-yl, 6-methylaminopurin-yl, yl, 6-dimethylaminopurin-9-yl, 2,6-diaminopurin-9-yl, 2,6-di(methylamino)purin-9-yl, 6-hydroxylaminopurin-9-yl, 7-deazaadenin-9-yl, 8-azaadenin-9-yl, 2-amino-6-chloropurin-9-yl, guanin-9-yl, 8-azaguanin-9-yl, 7-deazaguanin-9-yl, 6-thioguanin-9-yl, 6-methylthioguanin-9-yl, hypoxanthin-9-yl, 6-thiopurin-9-yl, and 6-methylthiopurin-9-yl; and the pharmaceutically acceptable salts of such compounds.

The process of the present invention for preparing the compounds of formulae Ic and Id is conveniently represented by the following schematic overall reaction equations:

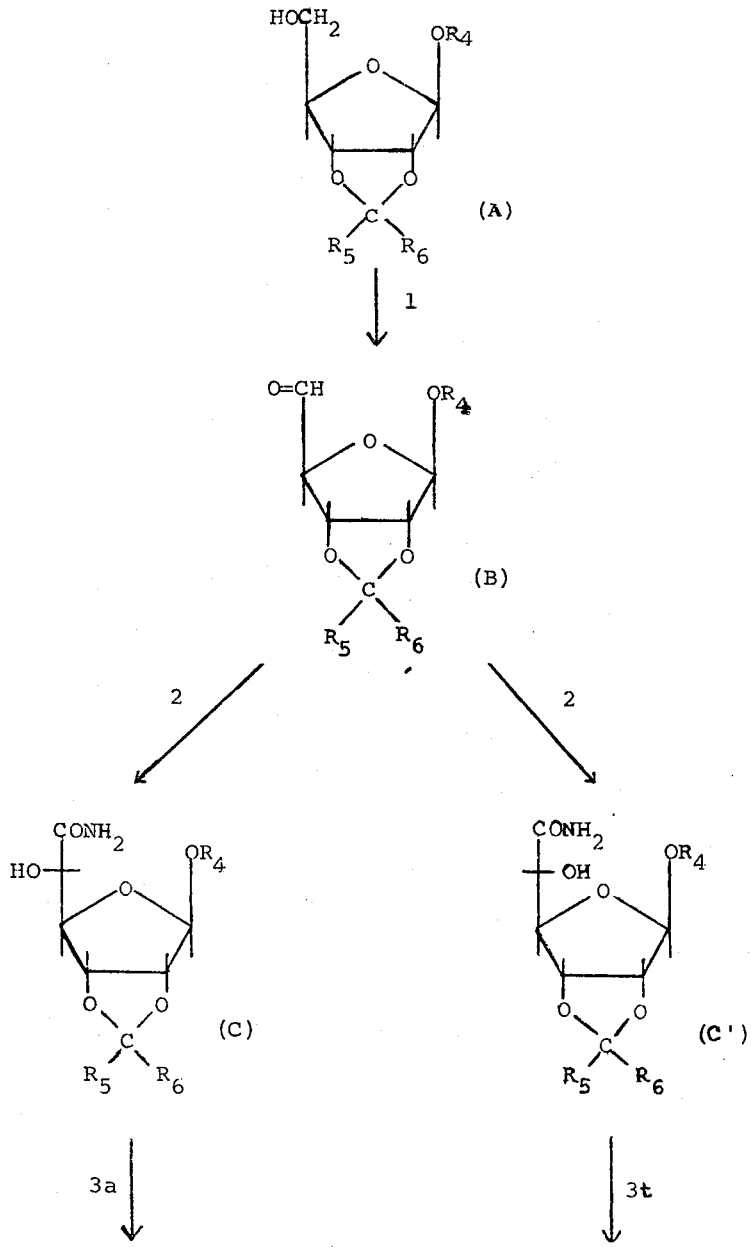

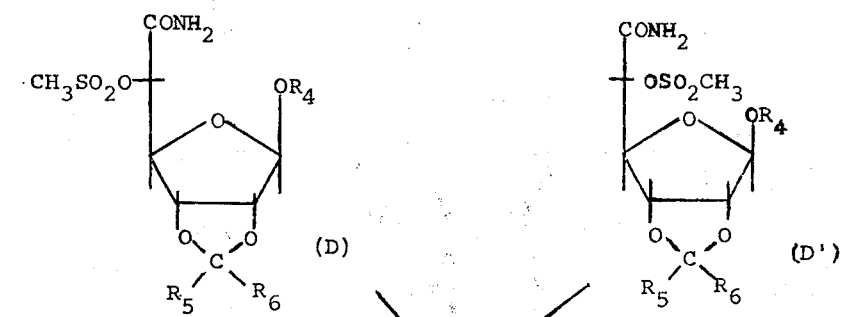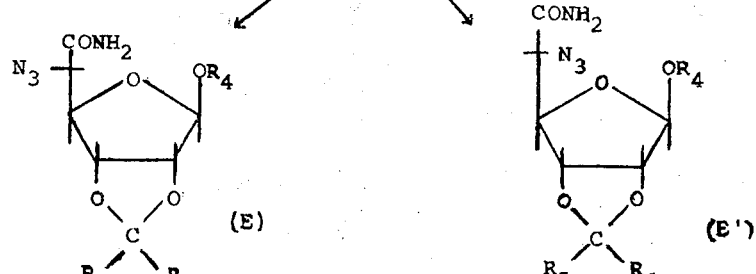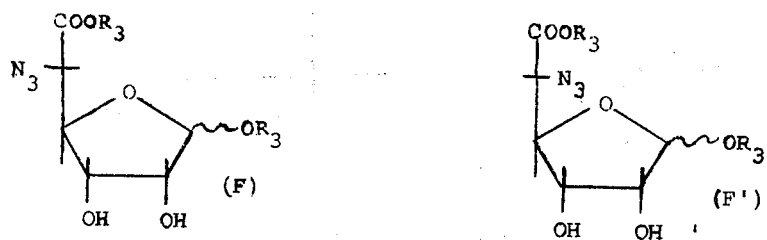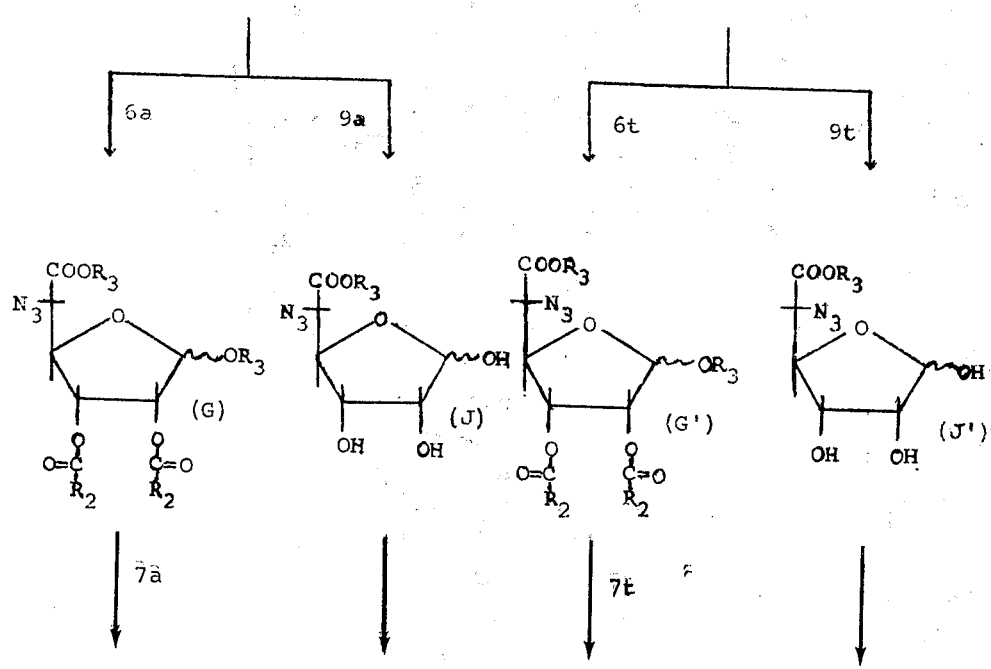

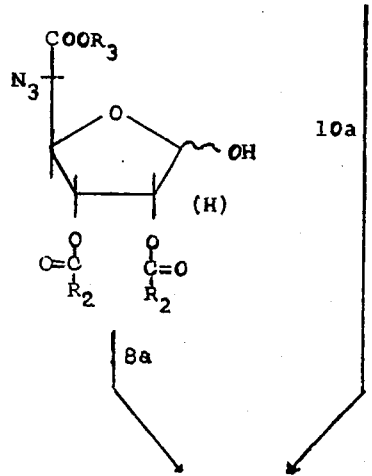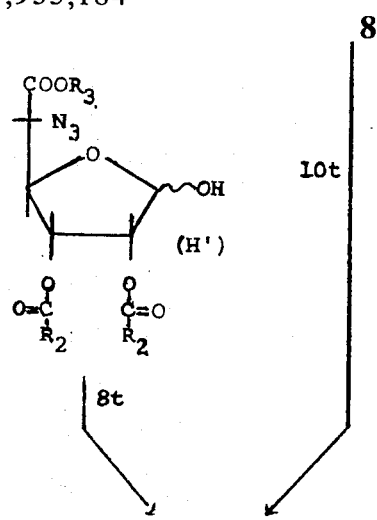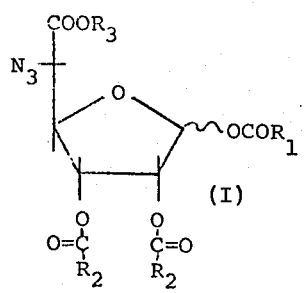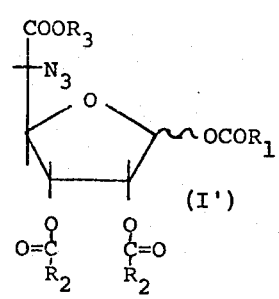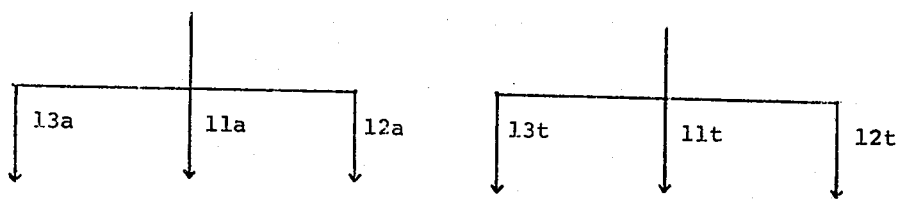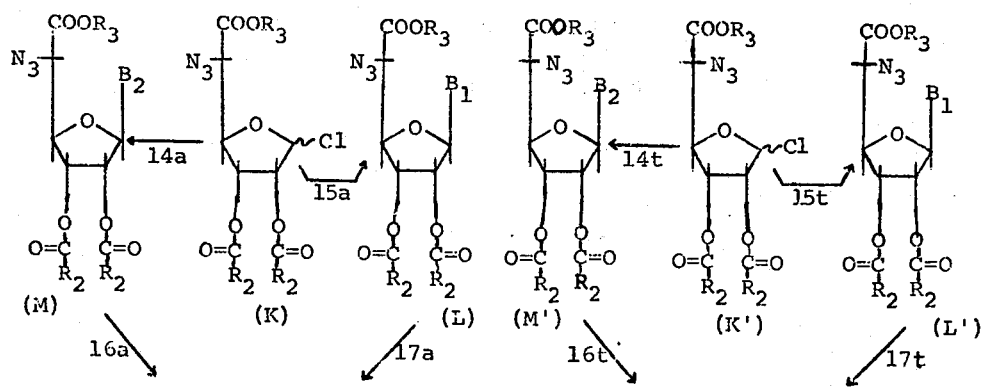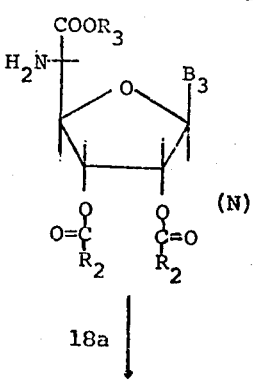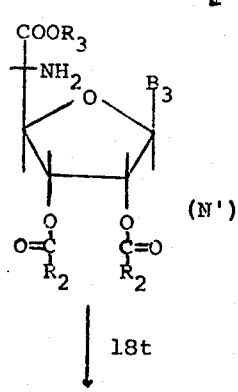

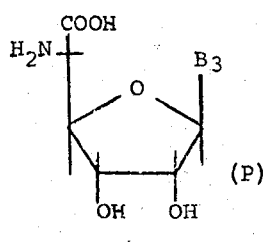
(P)

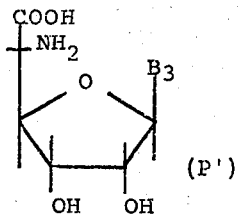
(P')

where $R_1$ and $R_2$ are lower alkyl radicals having one to six carbon atoms, phenyl radicals or substituted phenyl radicals; $R_3$ and $R_4$ are lower alkyl radicals having one to six carbon atoms; $R_5$ and $R_6$ are lower aklyl radicals having one to six carbon atoms or together with the carbon atom to which they are joined form a saturated cycloalkyl having from five to seven carbon ring atoms; $B_1$ is a pyrimidine radical; $B_2$ is a purine radical; and $B_3$ is either a pyrimidine or a purine radical.

In this schematic process flow chart, the $a$ series of steps corresponds to those individual steps wherein a β-D-allo compound is produced, the $t$ series of steps corresponds to those individual steps wherein an α-L-talo compound is produced, and compounds P and P' correspond to compounds Ic and Id, respectively, of the aforementioned co-pending application.

Considering the above process in greater detail, compound B can be prepared, as in Step 1, by any suitable procedure such as, for example, by the oxidation of a 1',2',3'-protected sugar 5'-alcohol (i.e., compound A) according to the procedure of Moffatt et al. U.S. Pat. No. 3,248,380.

Step 2 of the above process, the preparation of the α-L-talofuranosyluronamide and β-D-allofuranosyluronamide intermediates of Formulae C' and C, respectively, can be conveniently effected by treating the sugar-5'-aldehydes of Formula B with a suitable cyanide salt followed by treatment with hydrogen peroxide. This treatment is typically, and preferably, conducted in a mixture of water and a suitable inert organic solvent such as methanol and preferably in the presence of a suitable base such as, for example, potassium or sodium carbonate. The reaction with cyanide is typically conducted at temperatures in the range of about from −10° to 20°C and preferably from 0° to 5°C, using mole ratios in the range of about from 2 to 5 moles of cyanide salt per mole of compound B. However, temperature and mole ratios both above and below these ranges can also be used. Subsequent addition of an oxidizing agent such as, for example, hydrogen peroxide, leads to the formation of compounds C and C'. Typically, the oxidizing agent is added in the neighborhood of about from 5 to 30 minutes after the initial reactants are mixed. The total reaction time is typically in the range of about from 15 to 60 minutes. After the desired reaction has taken place, the reaction solution is neutralized to a pH of about 7 by the addition of a suitable acid, for example, acetic acid. The resulting product, an epimeric mixture of the respective intermediates of Formulae C and C', can be recovered by any suitable procedure such as, for example, fractional crystallization or chromatography on silicic acid. Suitable cyanide salts which can be used include, for example, sodium cyanide, potassium cyanide, ammonium cyanide, tetraethylammonium cyanide and the like. Suitable inert organic solvents which can be used include, for example, methanol, ethanol, dioxane, tetrahydrofuran and the like.

Suitable bases which can be used include, for example, potassium carbonate, sodium carbonate and the like. Suitable acids which can be used to neutralize the reaction mixture include, for example, acetic acid, Dowex 50 (H+) resin, Amberlite IRC-50 (H+) resin, phosphoric acid and the like.

The resulting epimeric mixture can be utilized in the next process step, but preferably the epimeric mixture is first resolved into its respective α-L-talo and β-D-allo isomers, which can then be individually subjected to the remaining steps of the above process. It has been found that by treating the respective isomers individually rather than as an epimeric mixture, cleaner products are ultimately obtained with less purification difficulties. Resolution of the respective L-talo and D-allo isomers can be effected by any suitable resolution procedure such as, for example, fractional crystallization, or chromatography or silicic acid.

The following discussion will be on the basis that at this point in the process the epimeric mixture is resolved into its two isomeric components.

Step 3 of the above process (i.e., steps 3a or 3t) can be conveniently effected by treating the corresponding intermediates of Formulae C and/or C' with a suitable alkylsulfonyl halide or arylsulfonyl halide in the presence of a suitable organic reaction media, e.g., pyridine, thereby affording the corresponding 5'-alkylsulfonyl or 5-arylsulfonyl derivatives of Formulae D or D', respectively. This treatment is typically conducted at temperatures in the range of about from −10° to 20°C and preferably in the range of about from 0° to 5°C for from about 5 to 24 hours, using mole ratios in the range of from about 0.5 to 1.0 moles of compound C or C' per mole of alkylsulfonyl halide or arylsulfonyl halide. However, temperatures, reaction times, and mole ratios both above and below these ranges can also be used. The resulting product of Formula D or D' can be isolated by any suitable procedure, such as crystallization or chromatography on silicic acid. Suitable alkylsulfonyl halides which can be used include, for example, methanesulfonyl chloride, ethanesulfonyl chloride and the like, and suitable arysulfonyl halides include benzenesulfonyl chloride, p-toluenesulfonyl chloride and p-bromobenzenesulfonyl chloride and the like. Suitable organic reaction media which can be used include, for example, dimethylformamide/triethylamine, and the like.

Step 4 of the above process (i.e., steps 4a or 4t) can be conveniently effected by treating the intermediates of Formulae D or D' with a suitable azide salt in a suitable inert organic media. This treatment effects an inversion of the 5'-substituent, thus the L-talo isomer of Formula D' affords the corresponding 5'-azido D-allo isomer of Formula E and correspondingly the D-allo isomer of Formula D affords the corresponding 5'-azido-L-talo isomer of Formula E'. This treatment is typically conducted at temperatures in the range of about from 50° to 90°C, for about from 4 to 16 hours, using mole ratios in the range of about from 2 to 5 moles of azide salt per mole of compound D or D'. However, temperatures, reaction times, and mole ratios both above and below these ranges can be used. Suitable azide salts which can be used include, for example, sodium azide, lithium azide, potassium azide, tetraethylammonium azide and the like. Suitable inert organic solvents which can be used include, for example, dimethylsulfoxide, dimethylformamide, dimethylacetamide, and the like. It has been found that good results are typically obtained by using sodium azide as the azide salt and dimethylformamide as the organic media. The resulting product of Formula E or E' can be separated from the reaction mass and further purified according to any suitable procedure, for example, crystallization or chromatography on silicic acid or alumina.

Step 5 of the above process (i.e., either step 5a or step 5t) can be conveniently effected by treating either compound E or E' with an aliphatic alcohol having one to six carbon atoms, such as methanol, in the presence of an acidic material, such as Dowex 50 (H+) resin. This treatment is typically conducted at elevated temperatures and conveniently under reflux, with stirring, for 4 to 16 hours. The lower aliphatic alcohol is also used as the solvent and is therefore usually in vast excess. However, reaction times, and temperatures both above and below these ranges can also be used. After removal of the resinous material by filtration, compound F or F', respectively, is isolated from the combined filtrates. Other lower aliphatic alcohols include ethanol, propanol, isopropanol, and the like.

Step 6 of the above process (i.e., step 6a or step 6t) can be conveniently effected by treating either compound F or F' with an acyl halide, such as acetyl chloride or benzoyl chloride, in an organic reaction media, such as dry pyridine. This treatment is typically conducted for about 4 hours to 24 hours using mole ratios in the range of from about 5 to 50 moles of acyl halide per mole of compound F or F'. This reaction is typically conducted at 0°C to 20°C. However, temperatures, reaction times, and mole ratios both above and below these can also be used. The reaction mixture is then treated with a lower aliphatic alcohol and the resulting ester removed. The resulting product of Formula G or G' respectively, can be isolated by any suitable procedure, such as, for example, crystallization or chromatography on silicic acid. Other liquid inert organic reaction media include, for example, dimethylformamide, dimethylacetamide in the presence of a base such as triethylamine or 2,6-lutidine.

Step 7 of the above process (i.e., step 7a or step 7t) can be conveniently effected by treating either compound G or compound G' with a strong aqueous acid, such as trifluoroacetic acid, for about 12 to 36 hours at 15°C to 25°C. However, temperatures and reaction times, both above and below these can also be used. Upon purification and concentration, the resulting product is either compound H or H', respectively. Other strong acids include sulfuric acid, Dowex 50 (H+) resin, trichloroacetic acid, hydrochloric acid, and the like.

Step 8 of the above process (i.e., step 8a or step 8t) can be conveniently effected by treating either compound H or H' with the anhydride of a carboxylic acid, such as the anhydride of acetic acid or the anhydride of another lower aliphatic acid having one to six carbon atoms, in an organic reaction media, such as pyridine. This treatment is typically conducted at temperatures in the range of from about 10°C to about 25°C using mole ratios in the range of about 5 to 50 moles of anhydride per mole of compound H or H'. However, temperatures, reaction times, and mole ratios both above and below these can also be used. Other organic reaction media include, for example, dimethylformamide in the presence of triethylamine. After purification and isolation, including, for example, chromatography on silicic acid, there is attained the novel intermediate I or I' of the present invention.

Step 9 of the above process (i.e., step 9a or step 9t) can be conveniently effected by treating either compound F or F' with a strong aqueous acid, such as trifluoroacetic acid, at temperatures from about 15°C to about 25°C for about 12 to 36 hours. However, temperatures and reaction times both above and below these can also be used. After purification and isolation, including removal of the strong acid, the resultant product is compound J or J'.

Step 10 of the above process (i.e., step 10a or step 10t) can be conveniently effected by treatment of either compound J or J' with an anhydride or acid chloride of a lower aliphatic or acomatic carboxylic acid, such as acetic anhydride, in the presence of an organic reaction media, such as pyridine, at temperatures in the range of from about 10°C to about 25°C for about 6 to 24 hours, using mole ratios in the range of about 5 to 50 moles of the anhydride per mole of compound J or J'. However, temperatures, reaction times, and mole ratios both above and below these can also be used. Other anhydrides include, for example, propionic anhydride, butyric anhydride, and the like. Other inert organic reaction media include, for example, dimethylformamide in the presence of triethylamine. After purification and isolation, including, for example, chromatography on silicic acid, there is obtained either compound I or I'.

Step 11 of the above process (i.e., step 11a or step 11t) can be conveniently effected by bubbling hydrogen chloride through a suspension of compound I or I' in an inert organic reaction media, such as anhydrous ether, until a clear solution is attained, followed by holding the solution for 12 to 72 hours at 0°C to 10°C. Isolation by evaporation results in compound K or K'. Other inert organic reaction media include, for example, methylene chloride, dioxane, and the like.

Step 12 of the above process (i.e., step 12a or step 12t) can be conveniently effected by reacting compound I or I' with a pyrimidine base material in an inert organic reaction media, such as 1,2-dichloroethane, in the presence of an appropriate catalyst, such as tin tetrachloride, titanium tetrachloride, BF$_3$-etherate, and the like, for 1 to 16 hours at 10°C to 25°C using 1 to 2 moles of the pyrimidine base material per mole of compound I or I'. After purification and isolation, including chromatography using silicic acid plates, there is obtained either compound L or L'. Other inert organic reaction media include, for example, benzene, acetonitrile, carbon disulfide, dimethylformamide, and the like. Pyrimidine base materials suitable for use in the present invention include the corresponding trimethylsilyl derivatives of:
  uracil
  5-fluorouracil
  5-chlorouracil
  5-bromouracil
  5-iodouracil 5-methyluracil
5-isopropyluracil
5-n-butyluracil
5-trifluoromethyluracil
5-hydroxymethyluracil
5-nitrouracil
5-methylaminouracil
5-dimethylaminouracil
6-azauracil
6-aza-5-methyluracil
5-aminouracil
5-azauracil
5-hydroxyuracil
cytosine
5-fluorocytosine
5-chlorocytosine
5-bromocytosine
5-iodocytosine
5-methylcytosine
5-isopropylcytosine
5-n-butylcytosine
5-trifluoromethylcytosine
5-hydroxymethylcytosine
5-nitrocytosine
5-methylaminocytosine
5-dimethylaminocytosine
6-azacytosine
6-aza-5-methylcytosine
5-aminocytosine
5-azacytosine
5-hydroxycytosine
2-thiouracil
2-thiocytosine
4-thiouracil Optionally, trimethylsilyl derivatives of N-acyl derivatives of the aforementioned cytosine and substituted cytosine compounds may also be used.

Compound L or L' can also be prepared from compound K or K', as by step 15a or 15t described below.

Step 13 of the above process (i.e., step 13a or step 13t) can be conveniently effected by reacting compound I or I' with a suitable purine base material in the presence of a strongly acidic catalyst such as di-p-nitrophenyl phosphroic acid, dichloroacetic acid, and the like at about 130° to 180°C for 5 to 30 minutes. Mole ratios in the range of from 1 to 2 moles of purine base material per mole of compound I or I' are used. However, temperatures, reaction times, and mole ratios both above and below these ranges can be used. After isolation and purification, including chromatography on silicic acid, the resultant product is compound M or M'.

Purine base materials suitable for use in the present invention include:
adenine
2-fluoroadenine
2-azaadenine
6-chloropurine
2,6-dichloropurine
6-methylaminopurine
6-dimethylaminopurine
2,6-diaminopurine
2,6-di(methylamino)purine
7-deazaadenine
8-azaadenine
8-azaguanine
guanine
7-deazaguanine
6-hydroxypurine
2-amino-6-chloropurine Optionally, the N-acylated derivatives of amino-substituted purines may also be used.

Compound M or M' can also be produced from compound K or K', as by step 14 as described below Step 14 of the above process (i.e., step 14a or step 14t) can be conveniently effected by treating either compound K or K' with a suitable substituted purine base material in an inert organic reaction media, such as benzene, in the presence of a suitable catalyst, such as mercuric cyanide. This treatment is typically conducted at elevated temperatures under reflux for 2 to 6 hours, using mole ratios in the range of from about 1 to 2 moles of the substituted purine base material per mole of compound K or K', after which the reaction mixture is cooled to room temperature. However, temperatures, reaction times, and mole ratios both above and below these ranges can be used. After purification and isolation, as by well-known procedures and techniques, there is obtained compound M or M'. Other inert organic reaction media include, for example, benzene, toluene, xylene, and the like. Suitable purine materials for use in this step 14 include, for example, the trimethylsilyl derivatives of the purine compounds listed above with respect to step 13.

Step 15 of the above process (i.e., step 15a or step 15t) can be conveniently effected by reacting compound K or K' with a suitable pyrimidine base material in an inert organic reaction media, such as benzene, in the presence of an approcatalyst, such as a suspension of mercuric oxide and mercuric chloride. This treatment is typically conducted at elevated temperatures under reflux for 2 to 6 hours, using mole ratios in the range of from about 1 to 2 moles of the substituted pyrimidine base material per mole of compound K or K', after which the reaction mixture is cooled to room temperature. However, temperatures, reaction times, and mole ratios both above and below these can be used. After purification and isolation, as by well-known procedures and techniques, there is obtained compound L or L'. Other inert organic reaction media include, for example, toluene, xylene, and the like. Suitable pyrimidine materials for use in the step 15 include, for example, those listed above with respect to step 12.

Steps 16 and 17 of the above process (i.e., step 16a or 16t; 17a or 17t) can be conveniently effected by hydrogenating a solution of compound M or M', or L or L', respectively, in the presence of a suitable catalyst, for example, a 5% palladium on barium sulfate mixture. This treatment is typically conducted at room temperature for 15 to 120 minutes. After purification and isolation, there is obtained compound N or N'. Alternatively, reduction can be done using reducing agents such as ammonium sulfide or sodium dithionite, if so desired.

Step 18 of the above process (i.e., step 18a or step 18t) can be conveniently effected by treating compound N or N' with a suitable base, such as barium hydroxide, in an inert organic reaction media, such as dioxane. This treatment is typically conducted at room temperature for 1 to 4 hours, using mole ratios in the range of from about 5 to 25 moles of the base per mole of compound N or N'. Temperatures, reaction times, and mole ratios both above and below these ranges can be used. After purification and isolation, there is obtained the uronic acid nucleoside P or P'.

In each of the process steps, described herein above and below, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation.

From the schematic flow chart diagrammed above and the more detailed explanation thereof also given above it can be seen that the intermediates I or I' can be converted in a minimum of three steps to the uronic acid nucleosides previously described in application Ser. No. 119,019, filed Feb, 25, 1971, or to the uronic acid nucleosides as described herein. Intermediates I or I' are, accordingly, valuable as a starting point from which a large variety of uronic acid nucleosides can be readily produced.

The compounds of this invention (i.e., compounds P or P') possess antibiotic, and in particular antifungal activity, as well as general antimetabolite activities, and thus are useful both as antifungal agents (e.g., agricultural fungicides) and also as sterilization agents where the conventional, more economical sterilization procedures are either ineffective or deleterious to organisms desired to be retained. The compounds of our invention are useful in containing or destroying undesired organisms in mammals.

The term pharmaceutically acceptable salts as used herein refers to those salts which do not adversely affect the pharamaceutical properties of the compounds of this invention, such as those salts conventionally used in the pharmaceutical art. Pharmaceutically acceptable salts include, for example, salts of inorganic acids such as, for example, sulfuric, sulfonic, sulfamic, nitric, phosphoric, hydrochloric acids and the like, and salts or organic acids such as, for example, acetic, citric, lactic, palmitic, tartaric, succinic, maleic, benzoic acids and the like; and also cation salts, such as, for example, sodium, potassium, ammonium, and the like.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

The following steps have been numbered to correspond to the steps identified in the schematic process flow chart above. The *a* series of steps are those individual steps wherein a D-allo compound is produced, and the *t* series of steps are those individual steps wherein an L-talo compound is produced.

Step 1

A solution of 0.98 g (0.01 mole) of anhydrous crystalline orthophosphoric acid in about 4 ml. of anhydrous dimethyl sulfoxide is added to a solution containing 4.08 g. (0.02 mole) of methyl 2',3'-0-isopropylidene-β-D-ribofuranoside (A; where $R_4$, $R_5$ and $R_6$ are methyl), 0.8 ml. (0.01 mole) of pyridine and 12.4 g (0.06 mole) of dicyclohexylcarbodiimide in 50 ml. of dimethyl sulfoxide. The exothermic reaction is maintained at 20°–25°C for 3 hours by occasional ice-cooling. After 3 hours, when the reaction is complete, the reaction mixture is diluted with 100 ml. of ethyl acetate, and a solution of 5.04 g (0.04 mole) of oxalic acid dihydrate in 10 ml. of methanol is added. The reaction mixture is poured into 200 ml. of a saturated aqueous sodium chloride solution, and the precipitated N,N'-dicyclohexylurea removed by filtration. The aqueous phase is separated and extracted with ethyl acetate. The organic phases are combined and washed with an aqueous sodium bicarbonate solution, a saturated aqueous sodium chloride solution, and ice water, dried over magnesium sulfate, concentrated to a syrup which is redissolved in 25 ml. of ethyl acetate, and filtered to remove any residual N,N'-dicyclohexylurea. Removal of the solvent yields 4.9 g. of a pale yellow syrup which is purified by sublimation at 60°–70°C (bath temperature) and 0.1 torr to give 2.3 g. of white crystalline methyl 2',3'-0-isopropylidene-β-D-ribo-pentodialdo-1',4'-furanoside (B).

Step 2

A solution of 6 g. (0.03 mole) of methyl 2',3'-0-isopropylidene-β-D-ribo-pentodialdo-1',4'-furanoside (B) in 60 ml. methanol is cooled to 0°C and added to a solution of 12 g. (0.024 mole) of sodium cyanide in 100 ml. of 5% aqueous sodium carbonate at 0°C. The mixture is stirred at 0°C for 60 minutes followed by the dropwise addition of 30 ml. of a 30% hydrogen peroxide solution over a 30-minute period during which time the reaction mixture is ice-cooled and vigorously stirred. After standing at 0°C for 60 minutes, the reaction mixture is treated successively with 300 ml. of ice-water and sufficient acetic acid to attain a pH of about 7. Sodium chloride is added to saturate the aqueous solution which is then extracted four times with 250 ml. portions of chloroform. The combined extracts are washed with aqueous sodium bicarbonate solution and brine, and then dried over magnesium sulfate. When evaporated to dryness, there is obtained 5.57 g. of a white crystalline residue which is a mixture of methyl 2',3'-0-isopropylidene-β-D-allofuranosiduronamide (C) and methyl 2',3'-0-isopropylidene-α-L-talofuranosiduronamide (C').

The crystalline mixture is dissolved in 20 ml. chloroform and applied to a 500 g. of column containing silica gel (deactivated with 6% water) prepared in chloroform. Elution with 2 liters of $CHCl_3$, 1 liter of 1% i-PrOH/$CHCl_3$, 1 liter of 2% i-PrOH/$CHCl_3$, 1 liter of 3% i-PrOH/$CHCl_3$, 1 liter of 4% i-PrOH/$CHCl_3$, 1 liter of 5% i-PrOH/$CHCl_3$, and 2 liters of 10% i-PrOH/$CHCl_3$, followed by pooling and concentration of the appropriate fractions, and crystallization from $CHCl_3$/hexane gave 2.28 g. of compound C and 2.23 g. of compound C', as defined above in this step 2.

Step 3a 2.46 ml of methanesulfonyl chloride is added dropwise to a solution of 5.95 g. (0.024 mole) of compound C in 100 ml. of pyridine while the solution is being cooled in an ice-salt bath. The solution is held at 4°C for 20 hours, then 20 ml. of water is added and, after standing at room temperature for 3 hours, the solution is evaporated to dryness. The residue is partitioned between 300 ml. of ethyl acetate and 100 ml. of a saturated aqueous sodium chloride solution. The ethyl acetate layer is washed with 100 ml. of brine and 50 ml. of water, dried over magnesium sulfate, and concentrated. Crystallization from chloroform/hexane gives 7.4 g. of methyl 2',3'-0-isopropylidene-5'-0-methanesulfonyl-β-D-allofuranosiduronamide (D).

Step 3t

The procedure of step 3a is repeated except compound C' is used in place of compound C. There is obtained 7.4 g. of methyl 2',3'-0-isopropylidene-5'-0-methanesulfonyl-α-L-talofuranosiduronamide (D').

Step 4a

A mixture of 7.48 g. (0.023 mole) of compound D' and 3.0 g. (0.046 mole) of sodium azide in 115 ml. of dry dimethylformamide is heated at 85°C, with stirring, for 20 hours. The reaction mixture is evaporated to dryness, water added, and the evaporation repeated. The residue is partitioned between 300 ml. of ethyl acetate and 100 ml. of saturated brine. The organic phase is further extracted twice with 100-ml. portions of brine, dride over magnesium sulfate, and concentrated to give 6.4 g. of a crude product. Crystallization from chloroform/hexane gives 5.1 g. of methyl 5'-azido-5'-deoxy-2',3'-0-isopropylidene-β-D-allofuranosiduronamide (E).

Step 4t

The procedure of step 4a is repeated except compound D is used in place of compound D'. There is obtained methyl 5'-azido-5'-deoxy-2',3'-0-isopropylidene-α-L-talofuranosiduronamide (E').

Step 5a

A solution of 1.36 g. (0.005 mole) of compound E in 60 ml. of dry methanol is heated under reflux, with magnetic stirring, for 5.5 hours in the presence of 7.5 g. of anhydrous Dowex 50 (H+) resin (a proprietary product of Dow Chemical Company, Midland, Mich., and being a sulfonic acid modified styrene polymer, 8% cross-linked with divinyl benzene). The resin is removed by filtration and washed well with methanol. The combined filtrates are concentrated to give methyl (methyl 5'-azido-5'-deoxy-D-allofuranosiduronate) (F; where $R_3$ is methyl).

Step 5t

The procedure of step 5a is repeated except compound E' is used in place of compound E. There is obtained methyl (methyl 5'-azido-5'-deoxy-L-talofuranosiduronate) (F'; where $R_3$ is methyl).

Step 6a

Compound F is dried by repeated (three times) evaporation of solutions thereof in 5 ml. of dry pyridine. The residue from the drying operation is dissolved in 10 ml. of pyridine, cooled to 0°C, and 3 ml. benzoyl chloride is added dropwise thereto, and the mixture held at 22°C for 18 hours. Methanol is then added to the cooled solution which is then evaporated to dryness. The residue is evaporated several times with water to remove methyl benzoate and partitioned between 50 ml. chloroform and 200 ml. of a saturated aqueous sodium bicarbonate solution. The aqueous layer is extracted three times with 50-ml. portions of chloroform. The combined extracts are dried over magnesium sulfate, concentrated and heated at 40°C under vacuum. The residue is dissolved in benzene and applied to a column containing 300 g. of silica gel (deactivated with 6% water) prepared in hexane. Elution with ether:hexane (1:3) gives 1.84 g. of methyl (methyl 5'-azido-2',-3'-di-0-benzoyl-D-allofuranosiduronate (G; where $R_2$ is phenyl and $R_3$ is methyl) as an anomeric mixture.

Step 6t

The procedure of step 6a is repeated except compound F' is used in place of compound F. There is obtained methyl (methyl 5'-azido-2',3'-di-0-benzoyl-5'-deoxy-L-talofuransiduronate) (G'; where $R_2$ is phenyl and $R_3$ is methyl), also as an anomeric mixture.

Step 7a

A solution of 1.57 g. (0.00346 mole) of compound G in 20 ml. of 90% trifluoroacetic acid is held at 22°C for 24 hours. The mixture is diluted with water, evaporated to dryness, and reevaporated twice more with water. The residue is dissolved in 100 ml. of chloroform, successively washed with a solution of sodium bicarbonate and water, dried over magnesium sulfate, and concentrated to give crude methyl (5'-azido-2',3'-di-0-benzoyl-5'-deoxy-D-allofuranosuronate) (H; where $R_2$ is phenyl and $R_3$ is methyl).

Step 7t

The procedure of step 7a is repeated except compound G' is used in place of compound G. There is obtained methyl (5'-azido-2',3'-di-0-benzoyl-5'-deoxy-L-talofuranosuronate) (H'; where $R_2$ is phenyl and $R_3$ is methyl).

Step 8a 1.3 g of compound H is dried by evaporation (three times) of solutions thereof in 20 ml. of dry pyridine, dissolved in 10 ml. of dry pyridine to which 4 ml. of acetic anhydride is added dropwise at 0°C, and held at 22°C for 18 hours. Methanol is then added with ice-cooling and the solution held for 2 hours at 22°C before it is evaporated to dryness, and then reevaporated twice more with water. The residue is dissolved in 75 ml. of ethyl acetate and the solution washed successively with a saturated solution of sodium bicarbonate and then water, dried over magnesium sulfate, and concentrated to give methyl (1'-O-acetyl-5'-azido-2',-3'-di-O-benzoyl-5'-deoxy-D-allofuranosuronate) ($I_b$; where $R_1$ and $R_3$ are methyl and $R_2$ is phenyl). This is dissolved in benzene and applied to a column containing 150 g. of silica gel prepared in benzene. Elution with hexane, followed by elution with ether:hexane (1:3) and ether:hexane (1:1) gives 710 mg. of compound $I_b$ above, as an anomeric mixture.

Step 8t

The procedure of step 8a is repeated except compound H' is used in place of compound H. There is obtained methyl (1'-O-acetyl-5'-azido-2',3'-di-O-benzoyl-5'-deoxy-L-talofuranosuronate) ($I'_b$; where $R_1$ and $R_3$ are methyl and $R_2$ is phenyl).

Step 9a

A solution of 0.249 g. (0.001 mole) of compound F in 5 ml. of 90% trifluoroacetic acid is held at 22°C for 24 hours. 10 ml. of water is added and the solution evaporated to dryness. Trifluoroacetic acid is removed by a co-evaporation (twice) with water, and the residue is triturated with ether to give methyl (5'-azido-5'-deoxy-D-allofuranosuronate) (J; where $R_3$ is methyl).

Step 9t

The procedure of step 9a is repeated except compound F' is used in place of compound F. There is obtained methyl (5'-azido-5'-deoxy-L-talofuranosuronate) (J'; where $R_3$ is methyl).

Step 10a 1 g. of compound J is dried by several evaporations of its solutions in 5 ml. portions of dry pyridine, dissolved in 5 ml. of pyridine to which 1.0 ml. of acetic anhydride is added. The resulting solution is held at 22°C for 16 hours. 5 ml. of methanol is added and the solution, after standing for 1 hour at 22°C, is evaporated to dryness. The residue is partitioned between 75 ml. of chloroform and 50 ml. of water, the organic phase being washed successively with 1N hydrochloric acid, a solution of sodium bicarbonate, and water, dried over magnesium sulfate, and concentrated to a pale yellow syrup. Chromatographic purification, as described in step 6a, gives methyl (1',2',3'-tri-O-acetyl-5'-azido-5'-deoxy-D-allofuranosuronate) ($I_a$; where $R_1$, $R_2$ and $R_3$ are methyl), as an anomeric mixture.

Step 10t

The procedure of step 10a is repeated except compound J' is used in place of compound J. There is obtained methyl (1',2',3'-tri-O-acetyl-5'-azido-5'-deoxy-L-talofuranosuronate) ($I'_a$; where $R_1$, $R_2$ and $R_3$ are methyl), as an anomeric mixture.

Step 11a

Dry hydrogen chloride is bubbled into a suspension of 2 g. of compounds $I_b$ in 15 ml. of dry ether until a clear solution is obtained. The solution is kept at 4°C for 18 hours and then evaporated to dryness. Repeated evaporation of benzene from the residue gives methyl(-5'-azido-2',3'-di-O-benzoyl-1'-chloro-1',5'-dideoxy-D-allofuranosuronate) ($K_b$; where $R_2$ is phenyl and $R_3$ is methyl.

The procedure of this step 11a is repeated except compound $I_a$ is used in place of compound $I_b$. There is obtained methyl(2',3'-di-O-acetyl-5'-azido-1'-chloro-1',5'-dideoxy-D-allofuranosuronate) ($K_a$; where $R_2$ and $R_3$ are methyl).

Step 11t

The procedure of step 11a is repeated except 2g. of compound $I'_b$ and 2 g. of compound $I'_a$ are used in place of the corresponding amounts of compounds $I_b$ and compound $I_a$, respectively. There is obtained methyl(5'-azido-2',3'-di-O-benzoyl-1'-chloro-1',5'-dideoxy-L-talofuranosuronate) ($K'_b$; where $R_2$ is phenyl and $R_3$ is methyl) or methyl (2',3'-di-O-acetyl-5'-azido-1'-chloro-1',5'-dideoxy-L-talofuranosuronate) ($K'_a$; where $R_2$ and $R_3$ are methyl), respectively.

Step 12a

A solution of 650 mg. (0.00135 mole) of compound $I_b$ and 380 mg. (0.00149 mole) of bis-trimethylsilyluracil in 20 ml. of 1,2-dichloroethane is treated with 0.23 ml. (0.00202 mole) of tin tetrachloride and the resulting solution held at 22°C for 22 hours. 20 ml. of a saturated sodium bicarbonate solution is then added followed by 50 ml. of chloroform. The organic phase is separated, filtered through Celite, dried over magnesium sulfate and concentrated. The residue is purified on two 1 meter × 20 cm. × 1.3 mm. silica-gel plates, which are developed with 10% methanol in chloroform. The major ultra-violet absorbing band is extracted with acetone to give 415 mg. of 1-(methyl 5'-azido-2',3'-di-O-benzoyl-5'-deoxy-β-D-allofuranosyluronate)uracil ($L_b$; where $R_2$ is phenyl, $R_3$ is methyl and $B_1$ is uracil-1-yl).

By replacing compound $L_b$ in this procedure with compound $I_a$, there is obtained 1-(methyl 2',3'-di-O-acetyl-5'-azido-5'-deoxy-β-D-allofuranosyluronate)uracil) ($L_a$; where $R_2$ and $R_3$ are methyl and $B_1$ is uracil-1-yl).

Step 12t

By following the procedure of step 12a but replacing compound $I_b$ with either compound $I'_b$ or compound $I'_a$ there is obtained 1-(methyl 5'-azido-2',3'-di-O-benzoyl-5'-deoxy-α-L-talofuranosyluronate)uracil ($L'_b$; where $R_2$ is phenyl, $R_3$ is methyl, and $B_1$ is uracil), and 1-(methyl 2',3'-di-O-acetyl-5'-azido'5'-deoxy-α-L-talofuranosyluronate)-uracil ($L'_a$; where $R_2$ and $R_3$ are methyl and $B_1$ is uracil-1-yl) respectively.

Step 13a

A mixture of 100 mg. of compounds $I_b$, 50 mg. of 6-chloropurine and 5 mg. of di-p-nitrophenylphosphoric acid is melted together at about 170°C for 15 minutes under vacuum at a pressure of 1 torr. The black melt is allowed to cool to room temperature, dissolved in chloroform and applied to a 1.3-mm. thick silica-gel plate which is eluted with 5% methanol/chloroform. The major ultra-violet absorbing band is extracted with acetone giving, after concentration, 9-(methyl 5'-azido-2',3'-di-O-benzoyl-5'-deoxy-β-D-allofuranosyluronate)-6-chloropurine ($M_b$; where $R_2$ is phenyl, $R_3$ is methyl, and $B_2$ is 6-chloropurin-9-yl) as a colorless foam.

By replacing compound $I_b$ in this procedure with compound $I_a$ there is obtained 9-(methyl 2',3'-di-O-acetyl-5'-azido-5'-deoxy-β-D-allofuranosyluronate)-6-chloropurine ($M_a$; where $R_2$ and $R_3$ are methyl, and $B_2$ is 6-chloropurin-9-yl).

Step 13t

By following the procedure of step 13a but replacing compound $I_b$ with either compound $I'_b$ or compound $I'_a$, there is obtained 9-(methyl 5'-azido-2',3'-di-O-benzoyl-5'-deoxy-α-L-talofuranosyluronate)-6-chloropurine ($M'_b$; where $R_2$ is phenyl, $R_3$ is methyl and $B_2$ is 6-chloropurin-9-yl) and 9-(methyl 2',3'-di-O-acetyl-5'-azidi'-5'-deoxy-a-L-talofuranosyluronate)-6-chloropurine ($M'_a$; where $R_2$ and $R_3$ are methyl and $B_2$ is 6-chloropurin-9-yl), respectively.

Step 14a

A stirred solution of 0.001 mole of compound $K_b$ and 250 mg. (0.0011 mole) of trimethylsilyl-6-chloropurine in 40 ml. of benzene is heated under reflux in the presence of 252 mg. (0.001 mole) of mercuric cyanide for 3 hours. The mixture is cooled to room temperature, 2 ml. of water and 10 ml. of methanol are added and the resulting solution concentrated. The residue is dissolved in chloroform, filtered through a bed of Celite, extracted with 20 ml. of a 30% potassium iodide solution and then extracted with 40 ml. of water. The aqueous extracts are extracted with 10 ml. of chloroform and the combined organic phases dried over magnesium sulfate and evaporated to dryness. The residue is purified on a 1 meter × 20 cm. × 1.3 mm. silica-gel plate which is eluted with 2% methanol in chloroform. The major band is eluted with acetone to give 390 mg. of compound $M_b$ as a non-crystalline foam.

By replacing compound $K_b$ in this procedure with compound $K_a$, there is obtained compound $M_a$.

Step 14t

By following the procedure of step 14a but replacing compound $K_b$ with either compound $K'_b$ or compound $K'_a$, there is obtained compound $M'_b$ or compound $M'_a$, respectively.

Step 15a

A solution of 0.001 mole of compound $K_b$ in 5 ml. benzene is added to a solution of 0.28 g. (0.0011 mole) bis-trimethylsilyluracil in 5 ml. benzene containing a suspension of 0.12 g. mercuric oxide and 0.12 g. mercuric chloride. The mixture is heated under reflux for 3 hours with magnetic stirring and then allowed to cool to room temperature. 5 ml. water and 5 ml. methanol are added and the mixture evaporated to dryness. The residue is treated with 25 ml. chloroform, and filtered through a bed of diatomaceous earth material (Celite). The filtrate is extracted with 10 ml. of 30% aqueous potassium iodide, 20 ml. saturated brine, two 30-ml. portions of water, and dried over magnesium sulfate. The drying agent is removed by filtration, the filtrate evaporated to dryness and the residue purified by preparative thick layer chromatography on a 1 meter × 20 cm. × 1.3 mm. silica-gel plate developed with 10% methanol in chloroform. The major ultra-violet absorbing band is extracted with acetone to give, after evaporation, compound $L_b$.

By replacing compound $K_b$ in this procedure with compound $K_a$, there is obtained compound $L_a$.

Step 15t

By following the procedure of step 15a but replacing compound $K_b$ with either $K'_b$ or $K'_a$, there is obtained compound $L'_b$ or $L'_a$, respectively.

Step 16a

A solution of 578 mg. (0.001 mole) of compound $M_b$ in methanol containing 2 ml. 1N hydrochloric acid is hydrogenated for 30 minutes at STP in the presence of 60 mg. of 5% palladium/barium sulfate. The mixture is filtered through a bed of Celite and the combined filtrates and washings evaporated to dryness. The residue is purified by chromatography on a 1 meter × 20 cm. × 1.3 mm. silica-gel plate developed with 12% methanol in chloroform. The product is eluted with acetone to give 9-(methyl 5'-amino-2',3'-di-O-benzoyl-5'-deoxy-$\beta$-D-allofuranosyluronate)-6-chloropurine ($N_{b_1}$; where $R_2$ is phenyl, $R_3$ is methyl, and $B_3$ is 6-chloropurin-9-yl).

By replacing compound $M_b$ in this procedure with compound $M_a$, there is obtained 9-(methyl 2',3'-di-O-acetyl-5'-amino-5'-deoxy-$\beta$-D-allofuranoxyluronate)-6-chloropurine ($N_{a_1}$; where $R_2$ and $R_3$ are methyl and $B_3$ is 6-chloropurin-9-yl).

Step 16t

By following the procedure of step 16a but replacing compound $M_b$ with either compound $M'_b$ or compound $M'_a$, there is obtained 9-(methyl 5'-amino-2',3'-di-O-benzoyl-5'-deoxy-$\alpha$-L-talofuranosyluronate)-6-chloropurine ($N'_{b_1}$; where $R_2$ is phenyl, $R_3$ is methyl and $B_3$ is 6-chloropurine) or 9-(methyl 5'-amino-2',3'-di-O-acetyl-5'-deoxy-$\alpha$-L-talofuranosyluronate)-6-chloropurine ($N'_a$; where $R_2$ and $R_3$ are methyl and $B_3$ is 6-chloropurin-9-yl), respectively.

Step 17a

A solution of 340 mg. (0.00635 mole) of compound $L_b$ in methanol containing 2 ml. of 1N hydrochloric acid is hydrogenated for 30 minutes at STP in the presence of 60 mg. of 5% palladium/barium sulfate. The mixture is filtered through a bed of Celite and the combined filtrate and washings evaporated to dryness. The residue is purified by chromatography on a 1 meter × 20 cm × 1.3 mm. silica-gel plate developed with 12% methanol in chloroform. The major product is eluted with acetone to give 1-(methyl 5'-amino-2',3'-di-O-benzoyl-5'-deoxy-$\beta$-D-allofuranosyluronate)uracil ($N_{b_2}$; where $R_2$ is phenyl, $R_3$ is methyl and $B_3$ is uracil-1-yl) as an amorphous solid.

By replacing compound $L_b$ in this procedure with compound $L_a$, there is obtained 1-(methyl 5'-amino-2',3'-di-O-acetyl-5'-deoxy-$\beta$-D-allofuranosyluronate)uracil ($N_{a_2}$; where $R_2$ and $R_3$ are methyl and $B_3$ is uracil-1-yl).

Step 17t

By following the procedure of step 17a but replacing compound $L_b$ with either compound $L'_b$ or compound $L'_a$, there is obtained 1-(methyl 5'-amino-2',3'-di-O-benzoyl-5'-deoxy-$\alpha$-L-talofuranosyluronate)uracil ($N'_{b_2}$; where $R_2$ is phenyl, $R_3$ is methyl and $B_3$ is uracil-1-yl) and 1-(methyl 5'-amino-2',3'-di-O-acetyl-5'-deoxy-$\alpha$-L-talofuranosyluronate)-uracil ($N'_{a_2}$; where $R_2$ and $R_3$ are methyl and $B_3$ is uracil-1-yl), respectively.

Step 18a

A solution of 75 mg. (0.14 mmole) of compound $N_{b_2}$ in 0.5 ml. of dioxane is added dropwise, with stirring, to 4 ml. of a saturated barium hydroxide solution. After standing for 3 hours at 22°C, the mixture is acidified with 1 ml. of concentrated hydrochloric acid and the clear solution is extracted three times with 5-ml. portions of ether. The aqueous phase is passed through a 30 cm × 1 cm column of Dowex 50 (H+) resin which is then washed with water until the eluate is low in ultraviolet absorbing material. The product is eluted with a 10% ammonium hydroxide solution giving, after concentration, 36 mg. of 1-(5'-amino-5'deoxy-$\beta$-D-allofuranosyluronic acid) uracil ($P_2$; where $B_3$ is uracil-1-yl).

By replacing compound $N_{b_2}$ in this procedure with compound $N_{a_2}$, there is also obtained compound $P_2$.

By replacing compound $N_{b_2}$ in this procedure with either compound $N_{b_1}$ or compound $N_{a_1}$, there is obtained 9-(5'-amino-5'-deoxy-$\beta$-D-allofuranosyluronic acid)-6-chloropurine ($P_1$; where $B_3$ is 6-chloropurin-9-yl).

Step 18t

By following the procedure of step 18a but replacing compound $N_b$ with either compound $N'_b$ or compounds $N'_a$, there is obtained 1-(5'-amino-5'-deoxy-$\alpha$-L-talofuranosyluronic acid) uracil ($P'_2$; where $B_3$ is uracil-1-yl).

By following the procedure of step 18a but replacing compound $N_b$ with either compound $N'_b$ or compound $N'_a$, there is obtained 9-(5'amino-5'-deoxy-$\alpha$-L-talofuranosyluronic acid)-6-chloropurine ($P'_1$; where $B_3$ is 6-chloropurin-9-yl).

The compounds referred to by letter in this specific example of the total process for producing the uronic acid nucleosides should be understood to mean the specific compounds produced, recited and identified therein, and not the more general compounds given the same identifying letters in the schematic process flow chart above.

In steps 16a and 16t, there is also produced 9-(methyl 5'-amino-2'-3'-di-O-benzoyl-5'-deoxy-β-D-allofuranosyluronate)-purine and 9-(methyl 5'-amino-2'-3'-di-O-benzoyl-5'-deoxy-α-L-talofuranosyluronate)-purine, respectively which can also be treated, in accordance with steps 17a and 18a, and steps 17t and 18t, respectively, to give 9-(5'-amino-5'-deoxy-β-D-allofuranosyluronic acid) purine ($P_1$; where $B_3$ is purin-9-yl) and 9-(5'-amino-5'-deoxy-α-L-talofuranosyluronic acid) purine ($P'_1$; where $B_3$ is purin-9-yl).

Starting with intermediate I, and by following the appropriate procedure of either steps 11a, 15a, 17a and 18a, or steps 12, 17a and 18a, utilizing, as will be apparent to one skilled in this art, an appropriately protected pyrimidine base material, the following 5'-amino-5'-deoxy-β-D-allofuranosyluronic acid nucleosides are prepared:

1-(5'-amino-5'-deoxy-β-D-allofuranosyluronic acid)-5-fluorouracil,
1-(5'-amino-5'-deoxy-β-D-allofuranosyluronic acid)-5-chlorouracil,
1-(5'-amino-5'-deoxy-β-D-allofuranosyluronic acid)-5-bromouracil,
1-(5'-amino-5'-deoxy-β-D-allofuranosyluronic acid)-5-iodouracil,
1-(5'-amino-5'-deoxy-β-D-allofuranosyluronic acid)-5-methyluracil,
1-(5'-amino-5'-deoxy-β-D-allofuranosyluronic acid)-5-isopropyluracil,
1-(5'-amino-5'-deoxy-β-D-allofuranosyluronic acid)-5-n-butyluracil,
1-(5'-amino-5'-deoxy-β-D-allofuranosyluronic acid)-5-trifluoromethyluracil,
1-(5'-amino-5'-deoxy-β-D-allofuranosyluronic acid)-5-hydroxymethyluracil,
1-(5'-amino-5'-deoxy-β-D-allofuranosyluronic acid)-5-nitrouracil,
1-(5'-amino-5'-deoxy-β-D-allofuranosyluronic acid)-5-methylaminouracil,
1-(5'-amino-5'-deoxy-β-D-allofuranosyluronic acid)-5-dimethylaminouracil,
1(5'-amino-5'-deoxy-β-D-allofuranosyluronic acid)-6-azauracil,
1-(5'-amino-5'-deoxy-β-D-allofuranosyluronic acid)-6-aza-5-methyluracil,
1-(5'-amino-5'-deoxy-β-D-allofuranosyluronic acid)-cytosine,
1-(5'-amino-5'-deoxy-β-D-allofuranosyluronic acid)-5-fluorocytosine,
1-(5'-amino-5'-deoxy-β-D-allofuranosyluronic acid)-5-chlorocytosine,
1-(5'-amino-5'-deoxy-β-D-allofuranosyluronic acid)-5-bromocytosine,
1-(5'-amino-5'-deoxy-β-D-allofuranosyluronic acid)-5-iodocytosine,
1-(5'-amino-5'-deoxy-β-D-allofuranosyluronic acid)-5-methylcytosine,
1-(5'-amino-5'-deoxy-β-D-allofuranosyluronic acid)-5-isopropylcytosine,
1-(5'-amino-5'-deoxy-β-D-allofuranosyluronic acid)-5-n-butylcytosine,
1-(5'-amino-5'-deoxy-β-D-allofuranosyluronic acid)-5-trifluoromethylcytosine,
1-(5'-amino-5'-deoxy-β-D-allofuranosyluronic acid)-5-hydroxymethylcytosine,
1-(5'-amino-5'-deoxy-β-D-allofuranosyluronic acid)-5-nitrocytosine,
1-(5'-amino-5'-deoxy-β-D-allofuranosyluronic acid)-5-methylaminocytosine,
1-(5'-amino-5'-deoxy-β-D-allofuranosyluronic acid)-5-dimethylaminocytosine,
1-(5'-amino-5'-deoxy-β-D-allofuranosyluronic acid)-6-azacytosine,
1-(5'-amino-5'-deoxy-β-D-allofuranosyluronic acid)-6-aza-5-methylcytosine,
1-(5'-amino-5'-deoxy-β-D-allofuranosyluronic acid)-5-aminouracil,
1-(5'-amino-5'-deoxy-β-D-allofuranosyluronic acid)-5-aminocytosine,
1-(5'-amino-5'-deoxy-β-D-allofuranosyluronic acid)-5-azauracil,
1-(5'-amino-5'-deoxy-β-D-allofuranosyluronic acid)-5-azacytosine,
1-(5'-amino-5'-deoxy-β-D-allofuranosyluronic acid)-5-hydroxyuracil,
1-(5'-amino-5'-deoxy-β-D-allofuranosyluronic acid)-hydroxycytosine,
1-(5'-amino-5'-deoxy-β-D-allofuranosyluronic acid)-2-thiouracil,
1-(5'-amino-5'-deoxy-β-D-allofuranosyluronic acid)-2-thiocytosine,
1-(5'-amino-5'-deoxy-β-D-allofuranosyluronic acid)-4-thiouracil.

Starting with intermediate I, and by following the appropriate procedure of either steps 11a, 14a, 16a and 18a, or steps 13a, 16a and 18a, utilizing, as will be apparent to one skilled in this art, an appropriately protected purine base material, the following 5'-amino-5'-deoxy-β-D-allofuranosyluronic acid nucleosides are prepared:

9-(5'-amino-5'-deoxy-β-D-allofuranosyluronic acid)-adenine,
9-(5'-amino-5'-deoxy-β-D-allofuranosyluronic acid)-2-fluoroadenine,
9-(5'-amino-5'-deoxy-β-D-allofuranosyluronic acid)-2-azaadenine,
9-(5'-amino-5'-deoxy-β-D-allofuranosyluronic acid)-6-methylaminopurine,
9-(5'-amino-5'-deoxy-β-D-allofuranosyluronic acid)-6-dimethylaminopurine,
9-(5'-amino-5'-deoxy-β-D-allofuranosyluronic acid)-7-deazaadenine,
9-(5'-amino-5'-deoxy-β-D-allofuranosyluronic acid)-8-azaadenine
9-(5'-amino-5'-deoxy-β-D-allofuranosyluronic acid)-hypoxanthine,
9-(5'-amino-5'-deoxy-β-D-allofuranosyluronic acid)-guanine,
9-(5'-amino-5'-deoxy-β-D-allofuranosyluronic acid)-8-azaguanine,
9-(5'-amino-5'-deoxy-β-D-allofuranosyluronic acid)-7-deazaguanine,
9-(5'-amino-5'-deoxy-β-D-allofuranosyluronic acid)-2,6-dichloropurine,
9-(5'-amino-5'-deoxy-β-D-allofuranosyluronic acid)-2,6-diaminopurine, 9-(5'-amino-5'-deoxy-β-D-allofuranosyluronic acid)-2-amino-6-chloropurine,
9-(5'-amino-5'-deoxy-β-D-allofuranosyluronic acid)-2,6-di(methylamino)purine,
9-(5'-amino-5'-deoxy-β-D-allofuranosyluronic acid)-6-chloropurine.

Starting with intermediate I', and by following the appropriate procedure of either steps 11t, 15t, 17t and 18t, or steps 12t, 17t and 18t, utilizing, as will be apparent to one skilled in this art, an appropriately protected pyrimidine base material, the following 5'-amino-5'-deoxy-α-L-talofuranosyluronic acid nucleosides are prepared:

1(5'-amino-5'-deoxy-α-L-talofuranosyluronic acid)-5-fluorouracil,
1(5'-amino-5'-deoxy-α-L-tolfuranosyluronic acid)-5-chlorouracil,
1-(5'-amino-5'-deoxy-α-L-talofuranosyluronic acid)-5-bromouracil,
1(5'-amino-5'-deoxy-α-L-talofuranosyluronic acid)-5-iodouracil,
1-(5'-amino-5'-deoxy-α-L-talofuranosyluronic acid)-5-isopropyluracil,
1-(5'-amino-5'-deoxy-α-L-talofuranosyluronic acid)-5-n-butyluracil,
1-(5'-amino-5'-deoxy-α-L-talofuranosyluronic acid)-5-trifluoromethyluracil,
1-(5'-amino-5'-deoxy-α-L-talofuranosyluronic acid)-5-hydroxymethyluracil,
1-(5'-amino-5'-deoxy-α-L-talofuranosyluronic acid)-5-nitrouracil,
1(5'-amino-5'-deoxy-α-L-talofuranosyluronic acid)-5-methylaminouracil,
1-(5'amino-5'-deoxy-α-L-talofuranosyluronic acid)-5-dimethylaminouracil,
1(5'-amino-5'-deoxy-α-L-talofuranosyluronic acid)-6-azauracil,
1(5'-amino-5'-deoxy-α-L-talofuranosyluronic acid)-6-aza-5-methyluracil,
1-(5'-amino-5'-deoxy-α-L-talofuranosyluronic acid)-cytosine,
1-(5'-amino-5'-deoxy-α-L-talofuranosyluronic acid)-5-fluorocytosine,
1-(5'-amino-5'-deoxy-α-L-talofuranosyluronic acid)-5-chlorocytosine,
1-(5'-amino-5'-deoxy-α-L-talofuranosyluronic acid)-5-hydroxymethylcytosine,
1(5'-amino-5'-deoxy-α-L-talofuranosyluronic acid)-5-bromocytosine,
1-(5'-amino-5'-deoxy-α-L-talofuranosyluronic acid)-5-iodocytosine,
1-(5'-amino-5'-deoxy-α-L-talofuranosyluronic acid)-5-methylcytosine,
1-(5'-amino-5'-deoxy-α-L-talofuranosyluronic acid)-5-isopropylcytosine,
1-(5'-amino-5'-deoxy-α-L-talofuranosyluronic acid)-5-n-butylcytosine,
1-(5'-amino-5'-deoxy-α-L-talofuranosyluronic acid)-5-trifluoromethylcytosine,
1-(5'-amino-5'-deoxy-α-L-talofuranosyluronic acid)-5-nitrocytosine,
1-(5'-amino-5'-deoxy-α-L-talofuranosyluronic acid)-5-methylaminocytosine,
1-(5'-amino-5'-deoxy-α-L-talofuranosyluronic acid)-5-dimethylaminocytosine,
1-(5'-amino-5'-deoxy-α-L-talofuranosyluronic acid)-6-azacytosine,
1-(5'-amino-5'-deoxy-α-L-talofuranosyluronic acid)-6-aza-5-methylcytosine,
1-(5'-amino-5'-deoxy-α-L-talofuranosyluronic acid)-5-aminouracil,
1(5'-amino-5'-deoxy-α-L-talofuranosyluronic acid)-5-aminocytosine,
1-(5'-amino-5'-deoxy-α-L-talofuranosyluronic acid)-5-azauracil,
1(5'amino-5'-deoxy-α-L-talofuranosyluronic acid)-5-azacytosine,
1-(5'-amino-5'-deoxy-α-L-talofuranosyluronic acid)-5-hydroxyuracil,
1-(5'-amino-5'-deoxy-α-L-talofuranosyluronic acid)-5-hydroxycytosine,
1-(5'-amino-5'-deoxy-α-L-talofuranosyluronic acid)-2-thiocuracil,
1(5'-amino-5'-deoxy-α-L-talofuranosyluronic acid)-2-thiocytosine,
1-(5'-amino-5'-deoxy-α-L-talofuranosyluronic acid)-4-thiouracil,
1(5'-amino-5'-deoxy-α-L-talofuranosyluronic acid)-5-methyluracil.

Starting with intermediate I', and by following the appropriate procedure of either steps 11t, 14t, 16t, and 18t, or steps 13t, 16t and 18t, utilizing, as will be apparent to one skilled in this art, an appropriately protected purine base material, the following 5'-amino-5'-deoxy-α-L-talofuranosyluronic acid nucleosides are prepared:

9-(5'-amino-5'-deoxy-α-L-talofuranosyluronic acid)-adenine,
9-(5'-amino-5'-deoxy-α-L-talofuranosyluronic acid)-2-fluoroadenine,
9-(5'-amino-5'-deoxy-α-L-talofuranosyluronic acid)-2-azaadenine,
9-(5'-amino-5'-deoxy-α-L-talofuranosyluronic acid)-6-methylaminopurine,
9-(5'-amino-5'-deoxy-α-L-talofuranosyluronic acid)-6-dimethylaminopurine,
9-(5'-amino-5'-deoxy-α-L-talofuranosyluronic acid)-7-deazaadenine,
9-(5'-amino-5'-deoxy-α-L-talofuranosyluronic acid)-8-azaadenine,
9-(5'-amino-5'-deoxy-α-L-talofuranosyluronic acid)-6-chloropurine,
9-(5'-amino-5'-deoxy-α-L-talofuranosyluronic acid)-hypoxanthine,
9-(5'-amino-5'-deoxy-α-L-talofuranosyluronic acid)-guanine,
9-(5'-amino-5'-deoxy-α-L-talofuranosyluronic acid)-8-azaguanine,
9-(5'-amino-5'-deoxy-α-L-talofuranosyluronic acid)-7-deazaguanine,
9-(5'-amino-5'-deoxy-α-L-talofuranosyluronic acid)-2,6-dichloropurine,
9-(5'-amino-5'-deoxy-α-L-talofuranosyluronic acid)-2,6-diaminopurine,
9-(5'-amino-5'-deoxy-α-L-talofuranosyluronic acid)-2-amino-6-chloropurine,
9-(5'-amino-5'-deoxy-α-L-talofuranosyluronic acid)-2,6-di(methylamino)purine.

With respect to a specific uronic acid nucleoside, it is expected that the appropriate, or most appropriate, of the above-described procedures to be followed to produce the particular uronic acid nucleoside desired will be apparent to one skilled in this art, or can readily be determined by routine experimentation. Additionally, certain modifications may be necessary or desirable to achieve certain procedural or chemical objectives, and it is expected that such modifications will also be apparent to one skilled in this art.

As an example of an appropriately protected base material, in step 13 it may be desirable, or necessary, to use an N-acylated purine to produce the desired compound M or M'. Where such a protected base material is utilized, it may also be necessary to treat compound P or P' with an agent, such as aqueous ammonium hydroxide, to remove the N-acyl groups.

Step 14a or step 14t may alternatively be conducted by using a heavy metal salt, such as a chloro-mercuri salt, of the purine base material, instead of the trimethylsilyl derivative as specifically shown above.

In certain instances it may be necessary, or desirable, to produce a desired uronic acid nucleoside by producing compound P or P' as above and then reacting either of those compounds with further reactants in one or more steps to produce the desired nucleoside. The final nucleoside will also have the general formula P or P' as given above, but one or more substituents in the purine or pyrimidine moiety will be modified by the additional reaction or reactions undertaken. Examples of such modification reactions are given in steps 19–21 below.

Step 19a

A mixture of 0.33 g. 9-(5'-amino-5'-deoxy-β-D-allofuranosyluronic acid)-6-chloropurine ($P_1$; where $B_3$ is 6-chloropurin-9-yl) and 0.10 g. thiourea in 15 ml. dimethylformide is heated at 100°C for 2 hours. The solvent is evaporated in vacuo and the residue crystallized from aqueous ethanol giving 9-(5'-amino-5'-deoxy-β-D-allofuranosyluronic acid)-6-mercaptopurine. By repeating this process but replacing the above compound with 9-(5'-amino-5'-deoxy-β-D-allofuranosyluronic acid)-2-amino-6-chloropurine ($P_1$; where $B_3$ is 2-amino-6-chloropurine-9-yl) there is obtained 9-(5'-amino-5'-deoxy-β-D-allofuranosyluronic acid)-2-amino-6-mercaptopurine.

Step 19t

By following the procedure of step 19a, but replacing compound $P_1$ where $B_3$ is 6-chloropurin-9-yl with either 9-(5'-amino-5'-deoxy-α-L-talofuranosyluronic acid)-6-chloropurine or 9-(5'-amino-5-deoxy-α-L-talofuranosyluronic acid)-2-amino-6-chloropurine, there is obtained the corresponding α-L-talo-6-mercaptopurine or α-L-talo-2-amino-6-mercaptopurine compound, respectively.

Step 20a

A stirred solution of 0.33 g. 9-(5'-amino-5'-deoxy-β-D-allofuranosyluronic acid)-6-mercaptopurine in 10 ml. of 0.1N sodium hydroxide is treated, dropwise, with 0.15 g. methyl iodide. After the addition is completed, the reaction is stirred at room temperature for 3 hours, chilled to about 5°C and neutralized with glacial acetic acid. Ethanol is then added and crystallization is induced by scratching with a glass rod giving 9-(5'-amino-5'-deoxy-β-D-allofuranosyluronic acid)-6-methylthiopurine.

By repeating this procedure but replacing the above 6-mercaptopurine compound with the corresponding 2-amino-6-mercaptopurine compound there is obtained the corresponding 2-amino-6-methylthiopurine compound.

Step 20t

By repeating the procedure of step 20a but replacing the above β-D-allo-6-mercaptopurine compound with either the corresponding α-L-talo-6-mercaptopurine or 2-amino-6-mercaptopurine compound there is obtained, respectively, either the corresponding α-L-talo-6-methylthiopurine or α-L-talo-2-amino-6-methylthiopurine derivative.

Step 21a

A solution of 0.33 g. 9-(5'-amino-5'-deoxy-β-D-allofuranosyluronic acid)-6-chloropurine in 15 ml. dimethylformamide containing an excess of anhydrous hydroxylamine is heated at 100°C for 12 hours. The solvent is evaporated in vacuo and the solid residue is crystallized from aqueous ethanol giving 9-(5'-amino-5'-deoxy-β-D-allofuranosyluronic acid)-6-hydroxylaminopurine ($P_1$; where $B_3$ is 6-hydroxylaminopurin-9-yl).

Step 21t

By repeating the procedure of step 21a but replacing the above β-D-allo compound with the corresponding α-L-talo compound there is obtained the corresponding α-L-talo compound where $B_3$ is 6-hydroxylaminopurin-9-yl.

Substituted phenyl radicals include, for example, a phenyl radical having one or more lower alkyl (1 to 6 carbon atoms), halo, nitro, alkoxy or dialkylamino substitutents on the aromatic ring, and include, for example, o-tolyl, m-tolyl, p-tolyl, 3,5-xylyl, pentamethylphenyl, p-chlorophenyl, p-bromophenyl, 2,4,6-trichlorophenyl, p-nitrophenyl, p-dimethylaminophenyl, p-methoxyphenyl, and the like.

While the present invention has been described with reference to specific embodiments thereof, it should be understood by those skilled in this art that various changes may be made and equivalents may be substituted without departing from the true spirit and scope of the invention. In addition, many modifications may be made to adopt a particular situation, material or composition of matter, process, process step or steps, or then-present objective to the spirit of this invention without departing from its essential teachings.

What is claimed is:

1. A compound having the formula:

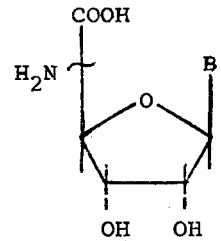

wherein the wavy line indicates either the 5'-D-allo or the 5'-L-talo epimer and B is a purine or pyrimidine radical selected from the group consisting of 5-hydroxyuracil-1-yl, 5-hydroxycytosin-1-yl, 5-azauracil-1-yl, 5-aza-cytosin-1-yl, 2-thiouracil-1-yl, 2-thiocytosin-1-yl, 4-thiouracil-1-yl, 2-amino-6-chloropurin-9-yl, 2-amino-6-mercaptopurin-9-yl, 6-methylthioguanin-9-yl, 6-chloropurin-9-yl, 2,6-dichloropurin-9-yl, 6-mercaptopurin-9-yl, 6-methylthiopurin-9-yl, and 6-hydroxylaminopurin-9-yl; and pharmaceutically acceptable salts thereof.

2. A compound having the formula:

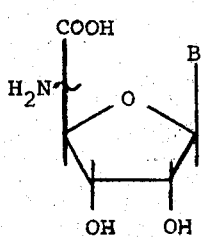

wherein the wavy line indicates either the 5'-D-allo or the 5'L-talo epimer and B is a purine radical selected from the group consisting of 6-chloropurin-9-yl, 2,6-dichloropurin-9-yl, 2-amino-6-chloropurin-9-yl, 2-amino-6-mercaptopurin-9-yl, 6-methylthioguanin-9-yl, 6-mercaptopurin-9-yl, 6-methylthiopurin-9-yl, and 6-hydroxylaminopurin-9-yl; and the pharmaceutically acceptable salts thereof.

3. A compound having the formula:

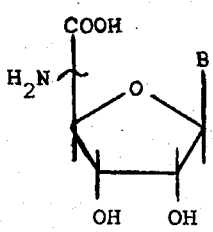

wherein the wavy line indicates either the 5'-D-allo or the 5'-L-talo epimer and B is a pyrimidine radical selected from the group consisting of 5-hydroxyuracil-1-yl, 5-hydroxycytosin-1-yl, 5-azauracil-1-yl, 5-azacytosin-1-yl, 2-thiouracil-1-yl, 2-thiocytosin-1-yl, and 4-thiouracil-1-yl; and the pharmaceutically acceptable salts thereof.

4. A compound having the formula:

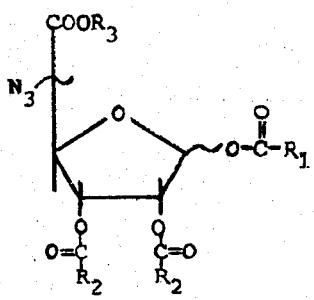

wherein the wavy line indicates either the 5'-D-allo or 5'-L-talo epimer; $R_1$ and $R_2$ are selected from the group consisting of lower alkyl radicals having one to six carbon atoms, phenyl and substituted phenyl radicals; and $R_3$ is a lower alkyl radical having one to four carbon atoms.

5. The compound of claim 4 wherein $R_1$ is a lower alkyl radical having one to six carbon atoms.

6. The compound of claim 5 wherein $R_2$ is a lower alkyl radical having one to six carbon atoms.

7. The compound of claim 5 wherein $R_2$ is a phenyl radical.

8. The compound of claim 4 wherein $R_1$ is a phenyl radical.

9. The compound of claim 8 wherein $R_2$ is a lower alkyl radical having one to six carbon atoms.

10. The compound of claim 8 wherein $R_2$ is a phenyl radical.

11. The 5'-D-allo epimer of the compound of claim 4.

12. The 5'-L-talo epimer of the compound of claim 4.

13. The 5'-D-allo epimer of the compound of claim 2.

14. The 5'-L-talo epimer of the compound of claim 2.

15. The 5'-L-talo epimer of the compound of claim 3.

16. The 5'-D-allo epimer of the compound of claim 3.

* * * * *